United States Patent [19]
Von Berg

[11] Patent Number: 5,556,136
[45] Date of Patent: Sep. 17, 1996

[54] CONNECTOR FOR FLEXIBLE MEDICAL TUBING

[76] Inventor: Peter Von Berg, 29 S. Ridge West, Tiburon, Calif. 94920

[21] Appl. No.: 428,912

[22] Filed: Apr. 25, 1995

[51] Int. Cl.⁶ .................................................. F16L 55/00
[52] U.S. Cl. ........................ 285/23; 285/242; 285/906
[58] Field of Search ............................ 285/12, 23, 38, 285/242, 906

[56] References Cited

U.S. PATENT DOCUMENTS

| | | | |
|---|---|---|---|
| 3,771,818 | 11/1973 | Weinhold | 285/242 |
| 4,635,972 | 1/1987 | Lyall | 285/242 |
| 4,775,173 | 10/1988 | Sauer | 285/242 X |
| 4,934,743 | 6/1990 | Kapgan et al. | 285/23 |
| 5,297,823 | 3/1994 | Dubost | 285/23 X |

FOREIGN PATENT DOCUMENTS

| | | | |
|---|---|---|---|
| 2644223 | 9/1990 | France | 285/23 |
| 2040260 | 2/1972 | Germany | 285/242 |
| 2217416 | 10/1989 | United Kingdom | 285/242 |

*Primary Examiner*—Dave W. Arola
*Attorney, Agent, or Firm*—Larry D. Johnson

[57] ABSTRACT

An improved connector apparatus for medical tubing includes a connector body, a tubing connector, a press ring or collar, and an articulating body/collar linkage. The body can be made as a male, female, or any other type of fitting or connector.

4 Claims, 3 Drawing Sheets

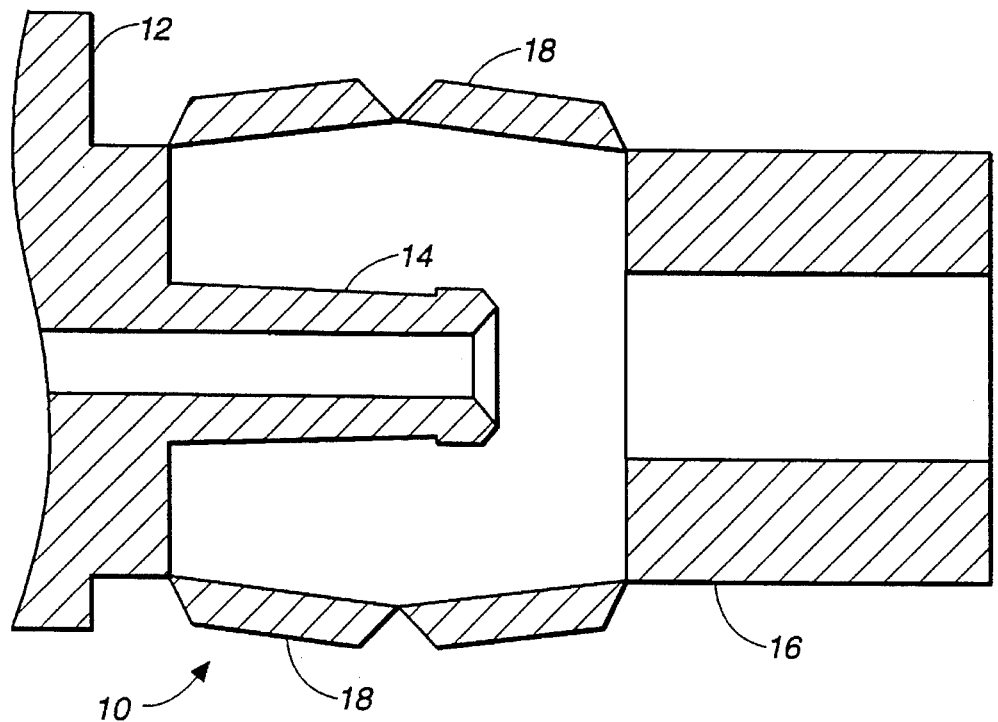
FIG._1
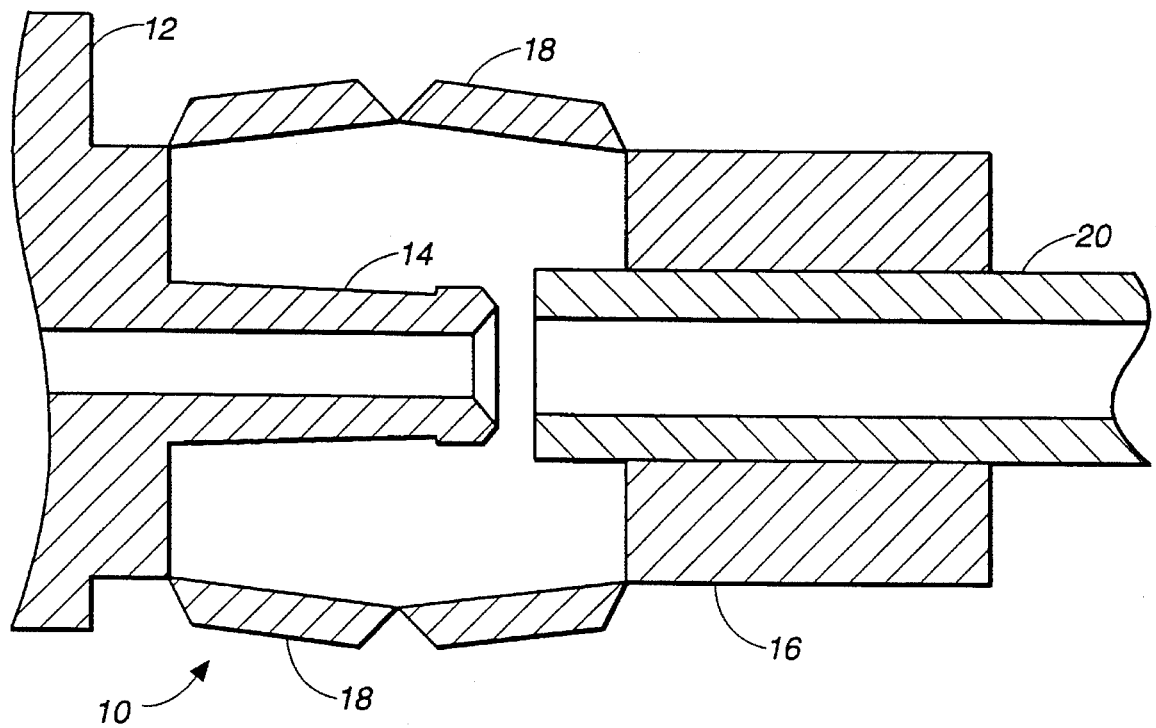
FIG._2

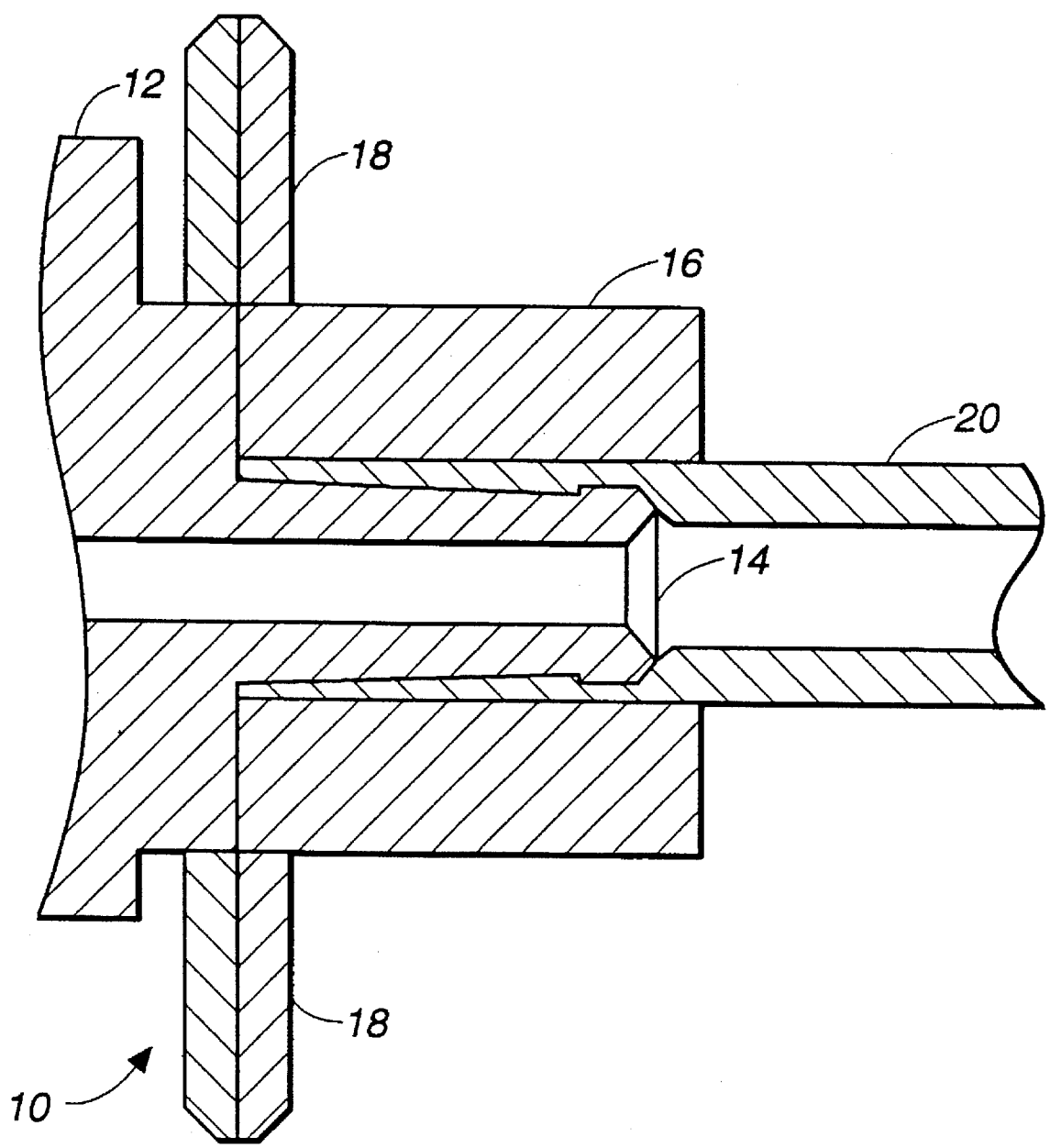
FIG._3

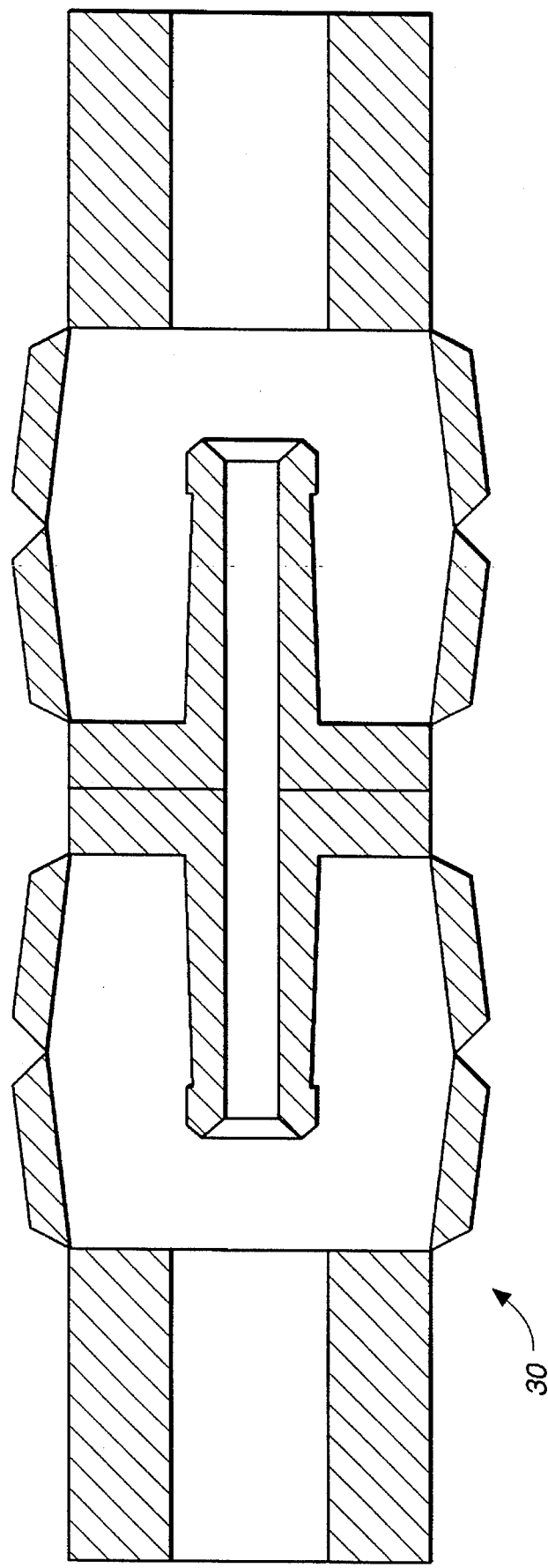
FIG._4

CONNECTOR FOR FLEXIBLE MEDICAL TUBING

BACKGROUND OF THE INVENTION

1. Field of the Invention

This invention relates generally to medical supplies and associated equipment, and more specifically to an improved connector apparatus for use with flexible medical tubing and the like.

2. Description of the Prior Art

Medical tubing is well known and in widespread use. It is often necessary to connect a segment of medical tubing to an article, or to another segment of tubing. Typically, these tubing connections are made through the use of solvent bonding, various adhesives (e.g., epoxy or UV-light curing glue), interference fits, heat forming, and molding (e.g., insert molding).

However, there are problems associated with all of these known methods of tubing connection. For example, solvent bonding generally is associated with the use of materials which may be considered hazardous in a medical environment, such as PVC. The use of these materials is often influenced by their low cost assembly made possible by the use of this bonding technique. Furthermore, bonding solvents can be hazardous in the manufacturing environment. In addition, PVC often can no longer be used in IV therapy due to today's pharmaceuticals, which may dissolve and "wash out" the softeners in the PVC, or themselves get absorbed in the plastic. Common adhesives require curing times, UV-light curable and hot-melt glues require special equipment and worker safety precautions, and molding requires a capital and labor intensive investment for its tooling and manufacture.

Some mechanical connection devices have been developed where you push the end of the tubing over a connector and secure it there with some form of clamp or other mechanical device. However, this generally requires that the connector and the securing device are separate parts, thereby increasing the cost of manufacture, and complicating the assembly.

It is accordingly an object of this invention to provide an apparatus to connect all types of medical tubing which replaces current connection methods, and which is not specific to the tubing or connector material in use.

It is a further object of this invention to provide a mechanical tubing connection apparatus capable of automating the tubing connection process by having all the required parts on one piece.

SUMMARY OF THE INVENTION

The connector for flexible medical tubing of this invention provides an improved connector apparatus for connecting a segment of medical tubing to an article or another segment of tubing. The inventive apparatus includes a connector body, a tubing connector, a press ring or collar, and an articulating body/collar linkage. The connector body can be made as a male luer-lock connector, female luer-lock connector, or any other type of connector.

BRIEF DESCRIPTION OF THE DRAWINGS

FIG. 1 is a side elevation cross-sectional view of a tubing-to-article embodiment of the connector for flexible medical tubing of this invention in its extended configuration and without tubing inserted or attached;

FIG. 2 is a side elevation cross-sectional view of the tubing-to-article connector of FIG. 1 in its extended configuration and with tubing inserted;

FIG. 3 is a side elevation cross-sectional view of the tubing-to-article connector of FIG. 2 in its compressed configuration to capture the inserted tubing; and FIG. 4 is a side elevation cross-sectional view of a tubing-to-tubing embodiment of the connector for flexible medical tubing of this invention in its extended configuration and without tubing inserted.

DETAILED DESCRIPTION OF A PREFERRED EMBODIMENT

FIG. 1 is a side elevation cross-sectional view of a tubing-to-article embodiment 10 of the connector for medical tubing of this invention in its extended configuration and without tubing inserted or attached. This view illustrates the component parts of this embodiment including a connector body portion 12, a tubing connector portion 14, a press ring or collar portion 16, and an articulating body/collar linkage portion 18. Body 12 can be made as a male, female, or any other type of connector or fitting (e.g., luer-lock, luer-slip, etc.).

FIG. 2 is a side elevation cross-sectional view of the tubing-to-article connector 10 of FIG. 1 in its extended configuration and with a segment of tubing 20 inserted within the collar portion 16.

FIG. 3 is a side elevation cross-sectional view of the tubing-to-article connector 10 of FIG. 2 in its compressed configuration to capture the segment of inserted tubing 20 by compressing it between connector portion 14 and collar portion 16. Articulating linkage portion 18 preferably consists of a pair of opposed, folding segments (for ease in manufacture), and can be constructed to stay on, or be removed after the tubing attachment is made.

FIG. 4 is a side elevation cross-sectional view of a tubing-to-tubing embodiment 30 of the connector for flexible medical tubing of this invention in its extended configuration and without tubing attached. In this embodiment, a pair of back-to-back (mirror image) body portion and collar portion units are created to "splice" separate tubing segments together in the manner described above. The two connection sides can have different diameters to enable connection of unlike sized tubing.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A connector for medical tubing comprising:

a connector body portion;

an articulating linkage member attached to said connector body portion;

a collar member attached to said articulating for axial movement relative to said connector body portion between an extended configuration and a compressing configuration, said collar member adapted for insertion onto a segment of tubing; and a tubing connector member attached to said connector body portion, said tubing connector member adapted for insertion into a segment of tubing;

wherein when a segment of tubing is inserted into said collar member in its extended configuration, said articulating linkage member enables said collar member to be axially moved toward said connector body portion and over said tubing connector member to its compressing configuration after inserting the segment of tubing onto said tubing connector member thereby capturing and compressing said segment of tubing between said collar member and said tubing connector member.

2. The connector for medical tubing of claim 1 wherein said articulating linkage member comprises a pair of opposed folding segments.

3. The connector for medical tubing of claim 1 wherein said connector body portion comprises a luer fitting.

4. The connector for medical tubing of claim 1 wherein said connector body portion comprises a pair of back-to-back tubing connector members adapted to splice separate tubing segments together.

* * * * *